United States Patent [19]
Ward

[11] 4,104,321
[45] Aug. 1, 1978

[54] PROCESS FOR THE SEPARATION OF OLEFINS

[75] Inventor: Dennis J. Ward, South Barrington, Ill.

[73] Assignee: UOP Inc., Des Plaines, Ill.

[21] Appl. No.: 779,414

[22] Filed: Mar. 18, 1977

[51] Int. Cl.² .......................... C07C 11/02; C07C 5/24
[52] U.S. Cl. .............................. 260/677 A; 260/683.2
[58] Field of Search ........................ 260/677 A, 683.2

[56] References Cited

U.S. PATENT DOCUMENTS

| | | | |
|---|---|---|---|
| 3,479,415 | 11/1969 | Shull | 260/683.2 |
| 3,800,003 | 3/1974 | Sobel | 260/683.2 |
| 3,821,123 | 6/1974 | Germanas et al. | 260/683.2 |

*Primary Examiner*—C. Davis
*Attorney, Agent, or Firm*—James R. Hoatson, Jr.; John G. Cutts, Jr.; William H. Page, II

[57] ABSTRACT

A butene mixture is separated to yield an n-butene rich product and an isobutylene rich product in a fractionator system. The fractionator reflux is isomerized before introduction into the fractionator. Other suitable olefins may be separated in a similar manner.

9 Claims, 1 Drawing Figure

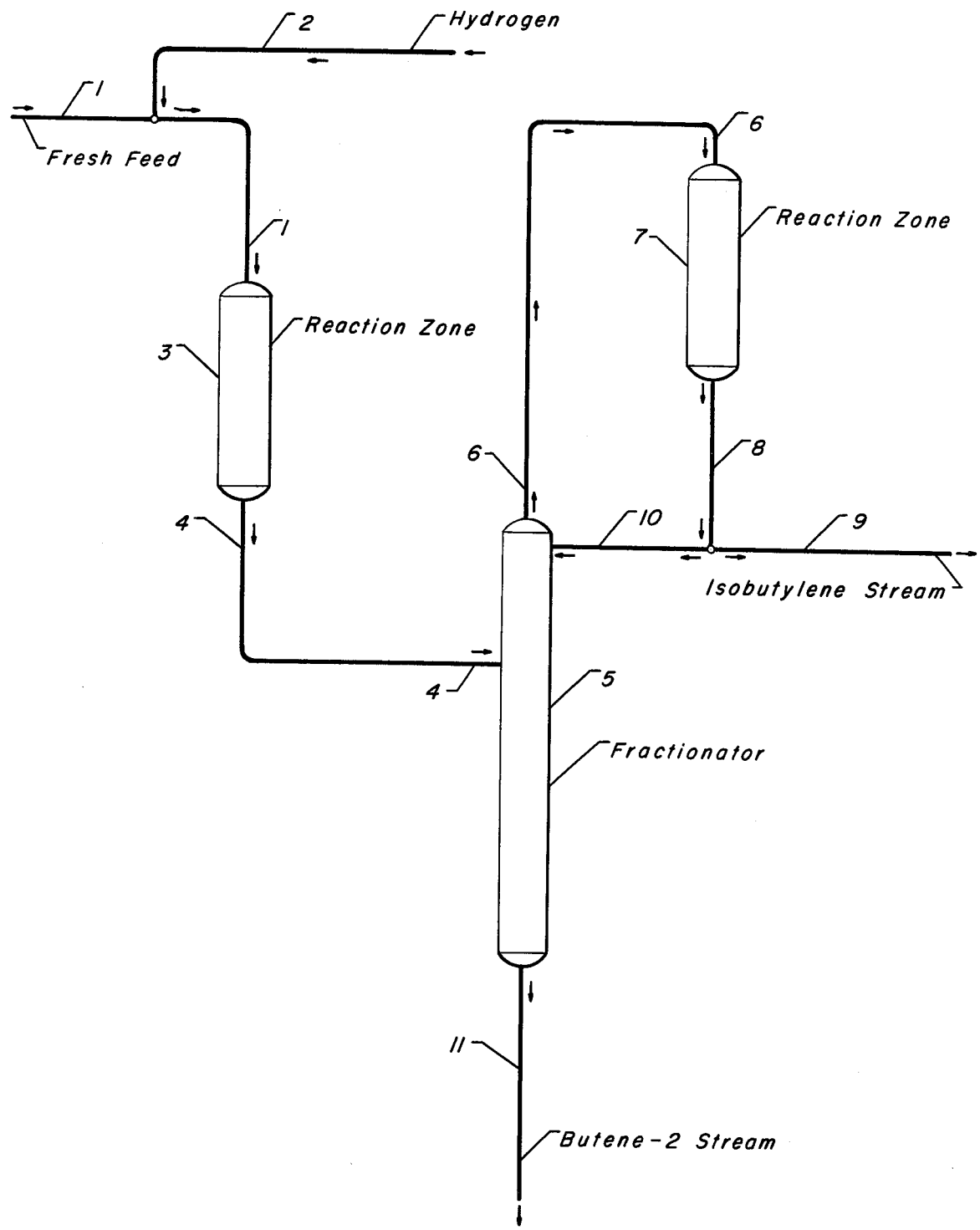

PROCESS FOR THE SEPARATION OF OLEFINS

BACKGROUND OF THE INVENTION

This invention relates to a process for the separation of a butene mixture to produce an n-butene rich product and an isobutylene rich product in a fractionator wherein the reflux is isomerized before introduction into the fractionator. The resulting high purity streams and isobutene are useful in subsequent reactions to produce secondary butyl alcohol and methyl ethyl ketone from normal butylene and butyl rubber and lubricating oil additive from isobutylene.

The isomerization of olefins is generally well known in the petroleum refining art. The double bond present in olefinic hydrocarbons shift readily over various catalysts to a more central position in the organic molecule. Composites of a metal from Group VIII of the Periodic Table properly inhibited in their hydrogenation activity with a refractory inorganic oxide as well known catalysts in producing olefinic bond migration.

SUMMARY OF THE INVENTION

It is an object of this invention to provide an economical method for isomerizing, and separating butene isomers via a novel fractionation and reaction process. In a broad embodiment, the present invention relates to a process for separating isoolefins and normal olefins from a mixture thereof which comprises the steps of: (a) separating said mixture into a first stream rich in normal olefins and a second stream rich in isoolefins in a fractionation zone; (b) reacting said second stream in an olefin isomerization zone; (c) returning at least a portion of the effluent from said isomerization zone to said fractionation zone as a reflux stream; (d) recovering at least a portion of the effluent from said isomerization zone as an isoolefin product stream; and (e) recovering a normal olefin product stream from said fractionation zone.

Another embodiment of the present invention relates to a process for producing isobutylene from a mixture containing normal butenes and isobutylene which comprises the steps of: (a) separating said mixture into a first stream rich in cis-2-butene and trans-2-butene and a second stream rich in isobutylene contaminated with 1-butene in a fractionation zone; (b) reacting said second stream in an olefin isomerization zone; (c) returning at least a portion of the effluent from said isomerization zone to said fractionation zone as a reflux stream; (d) recovering at least a portion of the effluent from said isomerization zone as an isobutylene product stream; and (e) recovering a normal butene product stream from said fractionation zone.

The normal boiling point of 1-butene is about 20° F. and the normal boiling point of isobutylene is about 19.6° F. These boiling points are quite close together, so that separating 1-butene from isobutylene by conventional fractionation is impractical. The normal boiling points of cis- and trans-2-butene are about 38.7° F. and 33.6° F., respectively, so that isobutylene and 1-butene can be separated from 2-butene by fractionation. Such a separation, however, is not capable of providing a high purity isobutylene stream, substantially free from 1-butene. By employing the method herein disclosed, 1-butene can be significantly reduced from an isobutylene product stream. Therefore, a high purity isobutylene product stream may be provided from a conventional source of butene isomer mixture.

Further objects, embodiments and illustrations indicative of the broad scope of the present invention will be apparent to those skilled in the art from the description of the drawing and preferred embodiments of the invention hereinafter provided.

DESCRIPTION OF THE DRAWING

The attached drawing is a schematic flow diagram and illustrates a particular embodiment of the present invention. Referring to the drawing, a conventional butylene feed, comprising 44 weight percent 1-butene, 44 weight percent isobutylene and 12 weight percent 2-butene, is charged through conduit 1 and hydrogen is charged through conduit 2. The combined butylene feed and hydrogen is passed via conduit 1 into reaction zone 3 which is maintained at olefin isomerization conditions. The hydrocarbons charged to reaction zone 3 are contacted with a fixed bed of an isomerization catalyst comprising nickel and sulfur on a porous carrier; the catalyst being prepared by forming an initial composite of the nickel carrier material, sulfiding and then stripping sulfur from the catalyst with hydrogen to provide a final isomerization catalyst. This catalyst hereafter being called a nickel subsulfide catalyst. The hydrocarbons are passed continuously through reaction zone 3 at a liquid hourly space velocity (volume of charge per volume of catalyst per hour) of about 0.1 to about 20, preferably in downward flow over the catalyst bed, and continuously withdrawn from reaction zone 3 through conduit 4. The isomerization reactor effluent in conduit 4 is charged to fractionator 5, which is conventional fractionation vessel. The isomerization reactor effluent has a reduced level of 1-butene with an essentially corresponding increased level of cis-2-butene and trans-2-butene. Because of a thermodynamic equilibrium constraint the 1-butene level will be at least five to fifteen percent of the normal butene fraction. In fractionator 5, a mixture of isobutylene and 1-butene is separated and withdrawn overhead through conduit 6. The mixture of hydrocarbons in conduit 6 passes to reaction zone 7 which is maintained at olefin isomerization conditions. The hydrocarbons charged to reaction zone 7 are contracted with a fixed bed of an isomerization catalyst comprising a nickel subsulfide catalytic material. The resulting isomerized hydrocarbons are continuously withdrawn from reaction zone 7 via conduit 8. At least a portion of said resulting isomerized hydrocarbons is returned via conduits 8 and 10 to fractionator 5 as reflux. The remainder of said resulting isomerized hydrocarbons is recovered via conduits 8 and 9 as an isobutylene product stream. Various conventional equipment and operations have not been described in the foregoing, such as pumps, valves, heat exchange means, etc. The use of such conventional equipment and operations will be understood to be essential and the method of their use in the process of the present invention will be obvious to those skilled in the art.

DETAILED DESCRIPTION OF THE INVENTION

The olefinic feedstock containing 1-butene, 2-butene and isobutylene employed in the present process may comprise solely butene isomers, or may contain other hydrocarbons. It is contemplated that the olefinic feed employed normally comprises a mixture of 1-butene, 2-butene and isobutylene. However, other materials may be present in olefin feedstock, including for example, paraffins, naphthenes or aromatics, as well as minor amounts of contaminants. A suitable olefinic feedstock may contain some propane, normal butane, isobutane, pentane, butadiene, etc. which hydrocarbons are often present in minor amounts in a conventional olefinic feedstock source. It is preferred, however, that the olefinic feedstock employed in the present process contain at least about 50 weight percent $C_4$ olefins.

The olefinic feedstock in the process of the present invention may first be contacted with an isomerization catalyst in an isomerization reaction zone at olefin isomerization conditions. Isomerization catalysts which can be employed in the isomerization operation of the present invention include catalysts which produce a shift of the olefinic bond in 1-butene to a more central position in the hydrocarbon molecules to form 2-butene. Various catalysts have been found suitable in prior art, including, for example, alumina, silica, zirconia, chromium oxide, boron oxide, thoria, magnesia, aluminum sulfate and combinations of two or more of the foregoing. Also employed have been acidic catalysts such as sulfuric acid, phosphoric acid, aluminum chloride, etc. either in solution or on a solid support. Also suitable for use in the isomerization operation as an isomerization catalyst is a sulfided nickel on porous carrier material such as described in U.S. Pat. No. 3,821,123. Thermal isomerization may be utilized, but suffers from the defects of producing excessive amounts of side products.

The preferred method by which the operation of the isomerization step of the present process may be effected in a continuous-type operation. One particular method is a fixed bed operation in which the feedstream comprising butene isomers is continuously charged to an isomerization reaction zone containing a fixed bed of catalyst, the reaction zone being maintained at olefin isomerization conditions including a temperature in the range from about 0° to about 400° F. or more, and a pressure of about 1 atmosphere to about 200 atmospheres or more. A preferred temperature is about 80° to about 300° F. and a preferred pressure is about 4 atmospheres to about 50 atmospheres. The charge of butene isomers is passed over the catalyst bed in either an upward or downward flow and withdrawn continuously and recovered. It is contemplated within the scope of the present invention that gases such as hydrogen, nitrogen, etc., may be continuously charged to the isomerization zone as desired.

Another continuous-type operation comprises a moving bed-type in which the butene isomers feed and the catalyst bed move co-currently or countercurrently to each other while passing through the isomerization zone.

Alternate but less efficient methods of achieving the same separations and product qualities are available. As an example, a system could be constructed employing the same reaction zone 3 and fractionator 5 illustrated in the drawing but with a second reaction zone on the net materials from the overhead of fractionation zone 5 and a second fractionation zone. For the same product qualities, however, more energy would be required because of the need for the second fractionation zone than required using the present invention.

Conventional sources of $C_4$ olefins contain a mixture of 1-butene, 2-butene and isobutylene. Although various attempts have been made in prior art to isomerize 1-butene by shifting the olefinic bond to provide 2-butene, it has been found, in general, that olefin isomerization conditions which favor economically desirable high conversion of 1-butene also tend to favor polymerization of isobutylene, a highly undesirable side reaction. Prior art has thus been limited to lower than optimum conditions of 1-butene to 2-butene when isobutylene is present in the feed stream to the isomerization operation. The process of the present invention at least partially overcomes the problems thereby created. In the present process, it is not necessary to maintain olefin isomerization conditions such that an extremely high conversion of 1-butene is achieved, so that polymerization of isobutylene is thereby avoided. At the same time, by charging the fractiontor overhead vapors containing 1-butene and isobutylene directly to an isomerization reaction zone and then refluxing at least a portion of the isomerized overhead to the fractionator, the concentration of 1-butene in the net overhead isobutylene product stream is significantly reduced. Other suitable olefins may be selected from pentenes, hexenes, etc.

The process of the present invention is further illustrated by the following examples. These examples are, however, not present to unduly limit the process of this invention, but to further illustrate the hereinabove described embodiments.

EXAMPLE I

A standard, conventional distillation column is charged with 10,000 mols per day of a mixed butene stream having the characteristics displayed in Table I.

TABLE I

|  | Feed | Overhead Product | Bottoms Product |
|---|---|---|---|
| 1-Butene, mols | 650 | 588 | 62 |
| Isobutylene, mols | 3500 | 3250 | 250 |
| cis-2-Butene, mols | 2925 | 6 | 2919 |
| trans-2-Butene, mols | 2925 | 36 | 2889 |

The distillation column contains at least 80 theoretical stages and is refluxed at about 80,000 mols/day. Inspections of the overhead and bottoms products are shown in Table I and indicate that the isobutylene overhead stream has a purity of 84% and that the 2-butene bottoms stream has a purity of 96%.

EXAMPLE II

The identical distillation column used in Example I is modified by incorporating an olefin isomerization reaction zone in the column's overhead vapor line. The feed to the above-described column as modified is charged with 10,000 mols per day of a mixed butene stream having the same characteristics as the Example I feed and displayed in Table II.

TABLE II

|  | Feed | Overhead Product | Bottoms Product |
|---|---|---|---|
| 1-Butene, mols | 650 | 26 | 44 |
| Isobutylene, mols | 3500 | 3241 | 259 |
| cis-2-Butene, mols | 2925 | 94 | 3147 |
| trans-2-Butene, mols | 2925 | 141 | 3048 |

Inspections of the overhead and bottoms products are shown in Table II and indicate that the isobutylene overhead stream has a purity of 93% and that the 2-butene bottoms stream has a purity of 96%.

From the foregoing examples, the beneficial import of the process of this invention is readily ascertainable by those skilled in the art.

I claim as my invention:

1. A process for the separation of isoolefin and normal olefin hydrocarbons from a mixture containing the same, which comprises the steps of:
   (a) subjecting said mixture to isomerization in a first isomerization zone to convert a portion of the normal olefin hydrocarbons to isoolefin;
   (b) fractionating the resultant isomerization zone effluent to separate the same into an isoolefin-rich stream containing normal olefin and a normal olefin-rich stream of reduced isoolefin content;
   (c) subjecting said isoolefin-rich stream to isomerization in a second isomerization zone to isomerize normal olefin hydrocarbons contained therein;
   (d) recovering an isoolefin product stream from the effluent of said second zone; and
   (e) separately recovering said normal olefin-rich stream from the aforesaid fractionating step (b).

2. The process of claim 1 further characterized in that said olefins are pentenes.

3. The process of claim 1 further characterized in that said olefins are hexenes.

4. The process of claim 1 further characterized in that said olefins are butenes.

5. The process of claim 1 further characterized in that said isomerization is catalyzed by a refractory inorganic oxide selected from alumina, silica, zirconia, chromium oxide and magnesia.

6. The process of claim 1 further characterized in that said isomerization is catalyzed by a partially sulfided nickel catalyst.

7. A process for producing isobutylene from a mixture containing normal butenes and isobutylene which comprises the steps of:
   (a) subjecting said mixture to isomerization in a first isomerization zone to isomerize a portion of the normal butenes contained therein;
   (b) fractionating the resultant effluent to separate the same into a first stream rich in cis-2-butene and trans-2-butene and a second stream rich in isobutylene containing 1-butene;
   (c) subjecting said second stream to isomerization in a second isomerization zone to isomerize butene-1 contained therein;
   (d) recovering at least a portion of the effluent from said second isomerization zone as an isobutylene product stream; and
   (e) separately recovering a normal butene product stream from the aforesaid fractionation step (b).

8. The process of claim 1 further characterized in that a portion of the effluent from said second isomerization zone is returned to fractionating step (b) as reflux therein.

9. The process of claim 7 further characterized in that a portion of the effluent from said second isomerization zone is returned to fractionating step (b) as reflux therein.

* * * * *